United States Patent [19]
Luchi

[11] 3,986,387
[45] Oct. 19, 1976

[54] SUPPORTING FIXTURES FOR PRESSURE-TESTING PIPE SECTIONS

[76] Inventor: Harry R. Luchi, Box 2242, Pasco, Wash. 99302

[22] Filed: Nov. 15, 1974

[21] Appl. No.: 524,207

[52] U.S. Cl. .................................. 73/49.8; 73/49.5
[51] Int. Cl.² .................................................. G01M 3/28
[58] Field of Search .................. 73/49.1, 49.5, 49.8; 138/90; 248/49

[56] References Cited
UNITED STATES PATENTS

| | | | |
|---|---|---|---|
| 1,099,158 | 6/1914 | Baker | 138/90 |
| 1,431,704 | 10/1922 | Smith | 73/49.1 |
| 2,403,859 | 7/1946 | Hatfield | 138/90 |
| 2,462,575 | 2/1949 | Walker | 138/90 X |
| 3,371,521 | 3/1968 | Hauk | 73/49.1 X |

Primary Examiner—Donald E. Watkins
Assistant Examiner—John S. Appleman
Attorney, Agent, or Firm—Wells, St. John & Roberts

[57] ABSTRACT

A supporting fixture for pipe to be pressure-tested. The fixture includes a cage-like structure to receive an elbow, the structure being composed of opposing cage-like cradle segments defining a pipe elbow enclosure. The ends of the segments have respective semicircular flange portions to which is bolted a disc for sealing the end of a pipe elbow received in the enclosure. In the case where the elbow has a length of pipe attached thereto, a two-segment retaining cage structure is employed for the free end portion of the pipe section, also having a disc bolted thereto for sealing the pipe, the segments of the said latter retaining cage structure being connected to the elbow cage by tie rods. In the case where two elbows are joined by an intervening length of pipe, two elbow-retaining cage structures are employed, connected by tie rods. The elbow cage segments may be hinged together.

9 Claims, 9 Drawing Figures

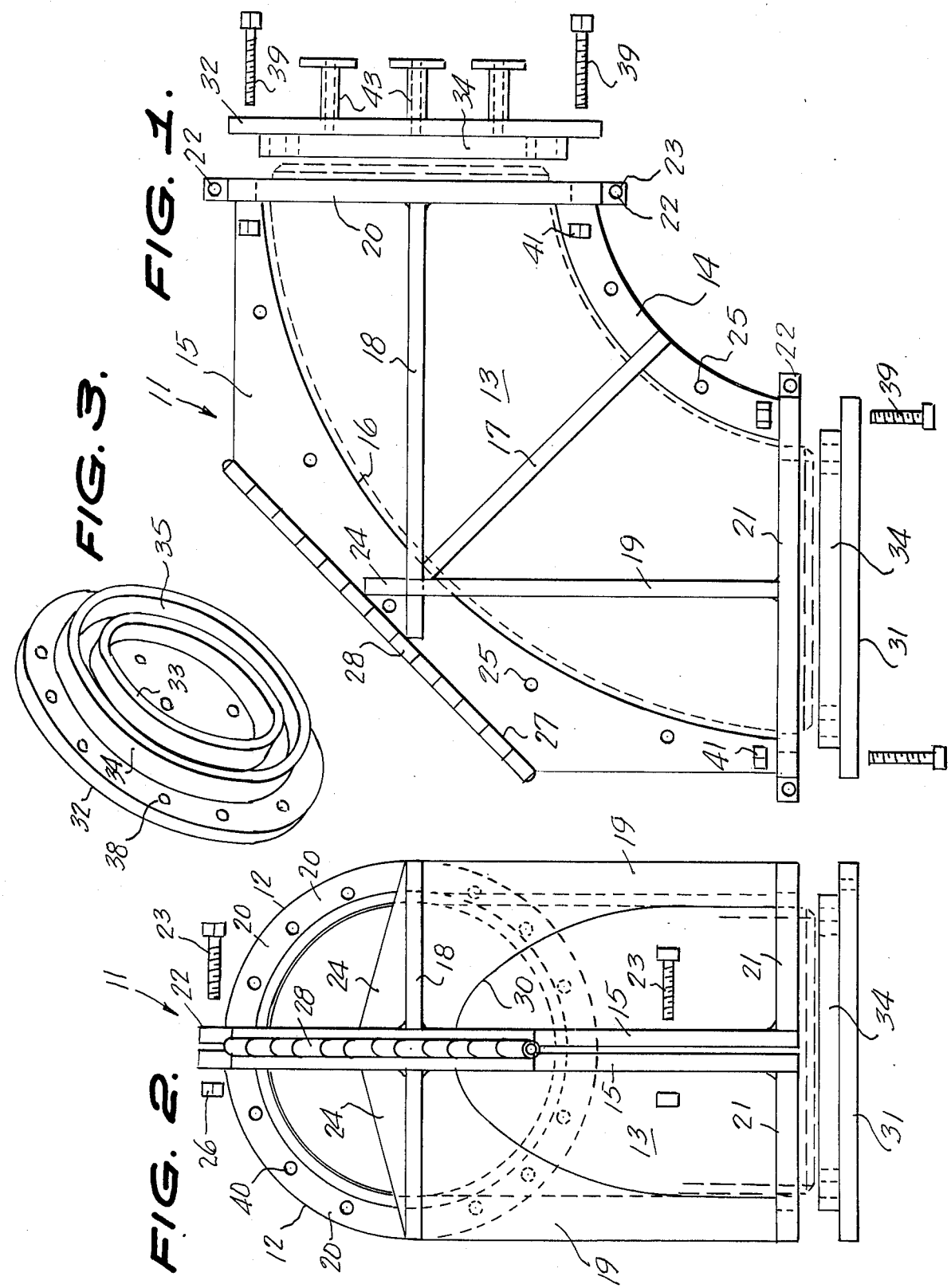

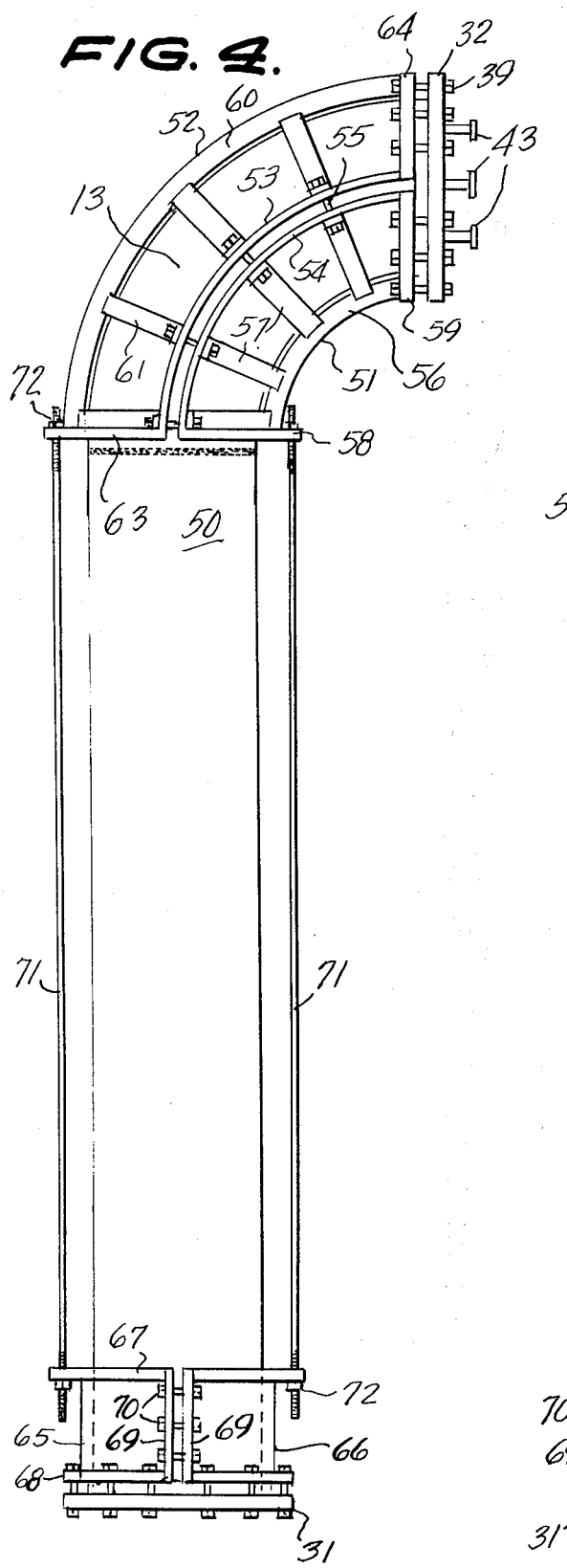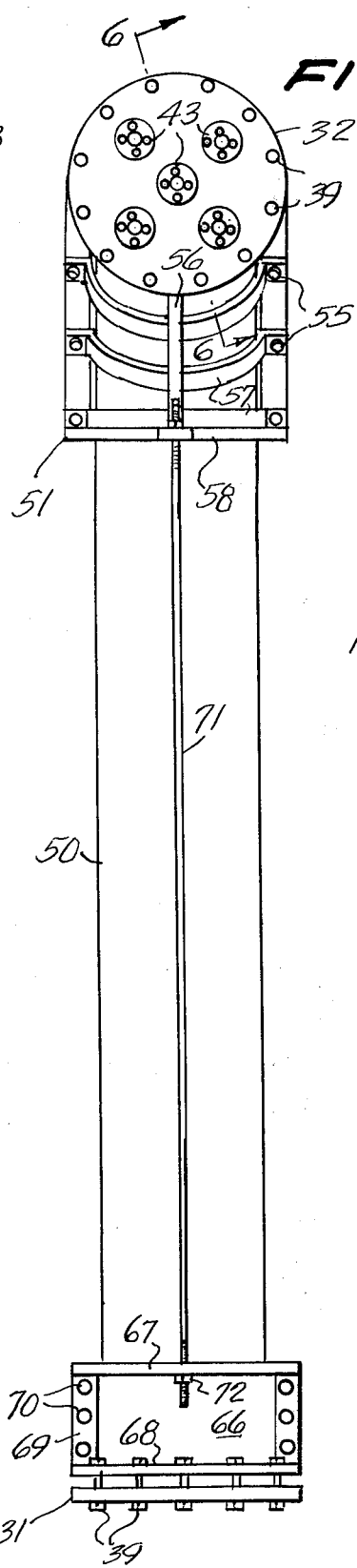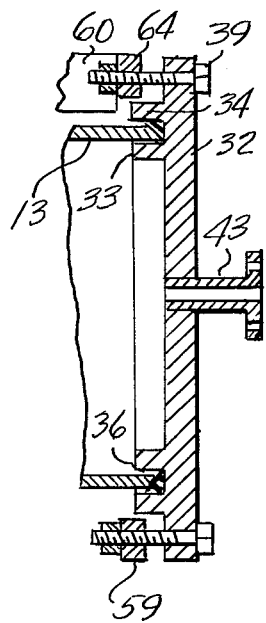

SUPPORTING FIXTURES FOR PRESSURE-TESTING PIPE SECTIONS

This invention relates to supporting fixtures for pressure-testing conduits, and more particularly to fixtures for supporting welded sections of pipe of various configurations, including one or more elbows, wherein the pipe sections must be sealed off in order to permit hydrostatic or vacuum testing of the sections.

A main object of the invention is to provide a novel and improved supporting fixture for pressure-testing pipe sections, the fixture being relatively simple to construction, being easy to set up for use, providing reliable sealing action, and eliminating the necessary of welding test flanges or test caps to the open ends of the section to be tested.

A further object of the invention is to provide an improved supporting fixture for pressure-testing elbows and other pipe sections, the fixture involving relatively inexpensive parts, being sturdy in construction, being able to resist large pressure forces, and making it unnecessary to weld flanges to the sections to be tested and to subsequently machine the ends of the sections after the tests have been completed.

A still further object of the invention is to provide an improved supporting fixture for sections of pipe of various different configurations, the fixture being provided with means for mechanically sealing the ends of the pipe section to be tested without requiring any welding operations on the sections, whereby the pipe is not weakened during the testing process.

Further objects and advantages of the invention will become apparent from the following description and claims, and from the accompanying drawings, wherein:

FIG. 1 is a top plan view of an improved supporting fixture for pressure-testing a pipe elbow, in accordance with the present invention.

FIG. 2 is an end elevational view of the fixture shown in FIG. 1.

FIG. 3 is a perspective view of one of the pipe end sealing flange members employed with the fixture of FIGS. 1 and 2.

FIG. 4 is a top plan view of a modified form of pipe testing fixture, in accordance with the present invention, arranged to accommodate a pipe elbow with a straight length of pipe welded thereto.

FIG. 5 is a front elevational view of the fixture shown in FIG. 4.

FIG. 6 is an enlarged cross-sectional view taken substantially on the line 6-6 of FIG. 5.

Figure 7:
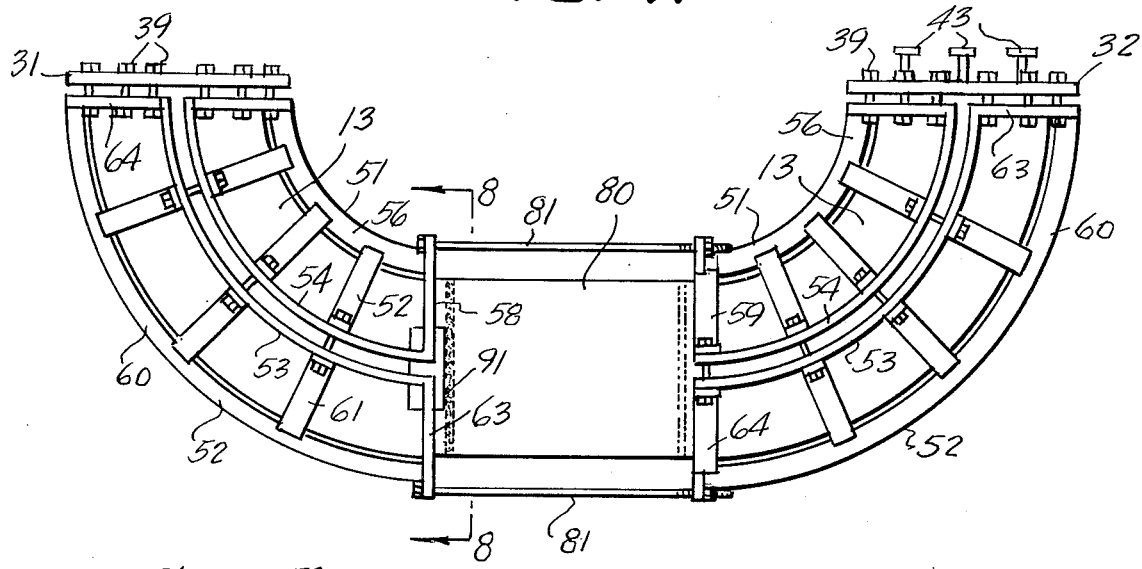
FIG. 7 is a top plan view of another form of pipe testing fixture according to the present invention, arranged to accommodate a pipe assembly including two elbows with a straight length of pipe welded therebetween.

The pipe fabrication industry is one which is concerned with fabricating pipe "spools," namely, assemblies of sections of pipe in desired configurations. By employing such prefabricated pipe assemblies, piping can be installed at the job site (such as in association with a nuclear reactor) at a considerably reduced cost as compared with assembling at the actual site. This lower cost is due to the fact that most fabrication processes can be improved because of more favorable working conditions found in a shop, as compared with the conditions found at the job site, and automatic loading equipment can be used. The pipe assemblies are normally fabricated to the maximum overall dimensions that can be shipped.

Job specifications sometimes require that pipe assemblies as above described by hydrostatically or vacuum-tested before they are shipped. In order to perform either type of testing, it is necessary that all openings in the assemblies be closed. The normal method heretofore used to make this closure is to weld test flanges or test caps to each of the open ends. The assemblies are then tested and the test flanges or test caps are cut off. After the cuts are made it is necessary to re-bevel the ends of the pipe assembly for welding at the job site. The molecular structure of the metal is changed in the heat-affected zones due to the welding heat. This change in molecular structure makes the weld areas the weakest part of the system. The welding heat also causes diametrical shrinkage in the weld areas.

A prime purpose of the present invention is to provide supporting fixtures for pipe testing which overcome the problems heretofore encountered in hydrostatic vacuum testing.

A more specific purpose of the improved pipe-testing fixtures of the present invention is to remove the necessity of exposing the pipe section end portions to more than one welding operation. With the use of temporary weld test caps, as heretofore employed, welding in this region creates a heat-affected zone which cannot be completely removed by re-beveling, because the amount which must be removed to eliminate the heat-affected zone will change the geometry of the weld fitting and its tangential dimension. Therefore, the heat-affected zone has heretofore been left after re-beveling, and when the fitting is re-welded into a piping system, it will contain portions which have been exposed to double effects of welding. This considerably weakens the system, since pipe system failures are most likely to occur in the heat-affected zones, as these are the weakest points in the welded system. Thus, the present invention aims to minimize metallurgical changes caused by welding temperatures and therefore will find valuable application in pipe systems which are exposed to high temperatures, nuclear corrosion, sodium corrosion, and physical conditions causing substantial expansion and contraction.

Pressure-testing pipe assemblies as above described may involve a pressure test using liquid as the test medium. The pipe spool or assembly, is closed off and filled with the test fluid. The pressure is then increased, at which point fluid will leak out of any voids which may be present. A leak will be detected by a loss of pressure or by observing the leak visually. Another type of test, namely, a vacuum test, employs negative pressure, namely, pressure below atmosphere pressure. All openings in the pipe spool are closed off and the air in the pipe spool is evacuated to a very low pressure. A leak is detected by the pressure reading on an associated vacuum gauge, showing an increase in the internal pressure in the pipe assembly under test.

Referring to the drawings, and more particularly to FIGS. 1, 2 and 3, 11 generally designates a typical supporting fixture for pressure-testing a pipe elbow section, in accordance with the present invention. The fixture 11 comprises a pair of cage-like cradle segments 12,12 formed to conformably receive a pipe elbow section 13 therebetween. Each cradle segment 12 comprises an inner arcuately curved longitudinal bar member or rib 14 and an outer curved longitudinal bar member or rib 15 which has an arcuately curved inner edge portion 16 concentric with the inner bar member 14 shaped to extend substantially parallel thereto and spaced therefrom to receive the elbow section 13 therebetween, as illustrated in FIG. 1. The bar members 14 and 15 are rigidly connected by an intermediate cross bar member 17, connected, as by welding, or the like, to the longitudinal bar member 15 at the junction of a pair of gusset plates 18 and 19 arranged at right angles to each other, as shown in FIG. 1. The ends of the bar members 14 and 15 are connected by respective semicircular end ring flange members 20 and 21 which have apertured end lugs 22, 22 to receive clamping bolts 23 to fasten the end flange members together with the elbow 13 received between the cradle segments, as will be presently explained. The gusset plate members 18 and 19 are respectively rigidly secured perpendicularly to the semicircular end ring flange members 20, 21, as by welding, or the like.

The corner portions of the gusset plates 18 and 19 may be suitably notched so that they can be interlocked prior to welding. A pair of triangular brace plates 24,24 may be welded to gusset plate 18 and longitudinal bar member 15 to provide suitable additional reinforcements. The longitudinal bar members 14 and 15 are provided with suitable bolt-receiving apertures 25 for receiving clamping bolts 23 to clampingly secure the cradle segments together with the elbow section 13 seated therebetween. The clamping bolts 23 are provided with fastening nuts 26, as shown in FIG. 2.

The members 15 have straight obliquely inclined top edge portions 27 and are hingedly connected together at said inclined top edge portions 27 by a linear hinge assembly 28. The hinge connection between the longitudinal bar members 15,15 provides automatic alignment of the cradle segments 12,12 for receiving an elbow section 13 therebetween. Thus, with the cradle segments in open relationship the pipe elbow section 13 may be placed in one of the cradle segments and then the other cradle segment may be rotated to closed position, after which the cradle segments may be fastened together by employing the clamping bolts 23 and nuts 26, as above described, the bolts being inserted through the registering apertures 25 of bars 14 and 15 and through the apertures of the lugs 22. As above mentioned, the bolts 23 are engaged with the nuts 26 to provide the closure and locking of the cradle segments around the pipe elbow section 13.

As shown in FIG. 2, the inner eges of the gusset plates 18 and 19 are conformably curved, for example, as shown at 30, to conform with the contour of the pipe elbow section 13.

Designated at 31 and 32 are respective end flange plate members which have pairs of concentric annular flange elements 33 and 34 rigidly secured thereto spaced to define annular seats 35 shaped to receive the ends of the pipe section 13 therein, each seat being provided with a resilient deformable sealing ring 36 (see FIG. 6) adapted to sealingly engage with the beveled end edges of the pipe section in the manner illustrated in FIG. 6. The end flange plate members 31 and 32 extend outwardly beyond their annular seats 35 to define securing marginal flange portions, said marginal flange portions being provided with apertures 38 to receive fastening bolts 39, the apertures 38 being registrable with apertures 40 provided in the semicircular ring flange members 20 and 21 so that the bolts 39 can be inserted therethrough, said bolts being provided with clamping nuts. With the end flange members 31 and 32 thus clampingly secured to the end flanges 21 and 20 of the cradle segments, the end flange members 31 can be tightened to seal the ends of the elbow section 13.

The end flange plate member 32 is provided with a plurality of conduit fittings 43 for making pressure-testing, fluid-tight communicative connections to the source of pressure-testing fluid, such as water under pressure or the like, a vacuum line, or other pressurized fluid medium, and also for making the required connections to gauges or other testing instruments required for a pressure test.

In operation, an elbow section 13 to be tested is placed between the cradle segments 12,12 after which the cradle segments are brought together and bolted around the pipe section 13 in the manner above described, and the end flange members 31 and 32 are then clampingly secured to the semicircular end ring flange portions 20 and 21 of the cradle segments in the manner above described to thus seal the ends of the pipe section by forcing said ends into sealing engagement with the resilient deformable sealing rings provided in the annular seats 35 in the manner illustrated in FIG. 6. The required connections are then made to the conduit fittings 43, and the test can then be made on the pipe section 13. The rigid cradle members prevent the elbow from bending deflection when the pipe section is pressurized. Without the cradle members the elbow has a tendency to try to straighten out placing undersirable stresses upon the elbow. It will be noted that this procedure does not require any welding operations on the ends of the pipe section thereby avoiding the creation of heat-affected zones and the disadvantages above described.

FIGS. 4, 5 and 6 illustrate a modified form of supporting fixture for pressure-testing pipe sections, designed for pipe sections comprising elbow portions 13 to which are welded straight pipe sections 50. The supporting fixture of FIGS. 4, 5 and 6, comprises a pair of arcuately curved cage-like cradle segments 51 and 52, shaped to receive the elbow 13 therebetween and having arcuately curved longitudinal bar members or ribs 53 and 54 which may be bolted together by bolts 55 in parallel relationship. The smaller cage segment 51 has an arcuately curved longitudinal inner bar member or rib 56 which is concentric with the outer arcuately curved bar members 54,54 thereof and which is rigidly connected thereto by a plurality of spaced radially extending semicircular cross bar members 57, the cradle segment 51 having semicircular end flange members 58 and 59. Similarly, the larger, or outer, cradle segment 52 is provided with an arcuately curved longitudinal bar member or rib 60 which is coaxial with respect to the arcuate bar members 53,53 thereof and which is rigidly connected thereto by the radial extending semicircular cross bar members 61. The cross bar members 61 extend in substantially the same radial plane as the cross bar members 57 of the inner cradle section 51. The outer cradle segment 52 is provided with respective semicircular end ring flange members 63 and 64 which lie substantially in the same radial planes as the respective end flange members 58 and 59 when the parts are assembles in the manner illustrated in FIG. 4.

An end flange plate member 32, similar to that illustrated in FIGS. 1 and 3, is connected to the semicircular end flanges 59 and 64 of cradle segments 51 and 52 in a manner similar to that described in connection with the embodiment illustrated in FIGS. 1, 2 and 3.

A pair of auxiliary cradle segments 65 and 66 are engaged around the end portion of the straight pipe section 50 said cradle segments being generally semicylindrical in shape and being provided with opposite end ring flanges 67 and 68. The cradle segments 65 and 66 are likewise provided at their longitudinal edges with longitudinally extending outwardly projecting flanges 69 which are clampingly connected together by fastening bolts 70 in the manner illustrated in FIGS. 4 and 5. A generally circular end flange plate member 31, similar to that above described, is bolted to the end flange members 68 of the cradle segments by bolts 39, the end of the straight pipe section 50 being sealingly engaged in the annular seat 35 of end flange member 31 in the same manner as above described in connection with FIGS. 1, 2 and 3. The ring flanges 67 and 63 are connected by longitudinal tie bars 71 on opposite sides of the straight pipe section 50 in the manner shown in FIG. 4, the tie bars 71 being threaded at their end portions and being provided with tightening nuts 72 to develop sufficient tension in the tie bars to draw the ends of the pipe section into sealing engagement with the resilient deformable gaskets provided in their respective annular seats 35 of the end flange members 31 and 32.

In using the fixture shown in FIGS. 4, 5 and 6, the cradle segments 51 and 52 are secured on the elbow portion 13 of the composite pipe section and the auxiliary cradle segments 65 and 66 are secured on the opposite end portion of the straight pipe section 50. The end flange plate members 32 and 31 are then secured to the ends of the respective pairs of cradle segments, in the manner above described, after which the cradle segments 51, 52 and 66, 65 are connected together by the longitudinal tie bars 71, which then are tensioned by tightening their nuts 72 to provide the required end seals of the composite pipe section. Alternatively, said end seals may be achieved by tightening the fastening bolts 39 associated with the end flange plate members 31, 32. After the composite part section has been thus sealingly mounted in the fixture, the necessary connections may be made to the pressurizing fluid and to the required instruments, thereby the pressure test can be then performed.

Figure 9:
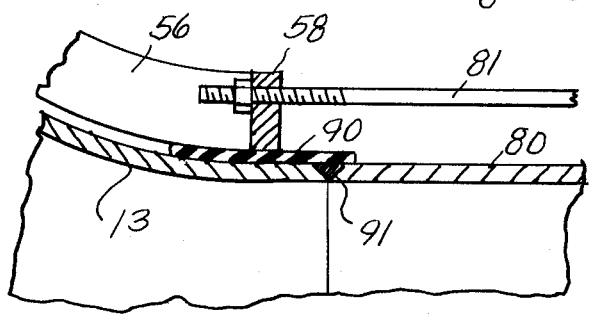
FIG. 9 is an enlarged fragmentary vertical cross-sectional view taken substantially on the line 9—9 of FIG. 8
Figure 8:
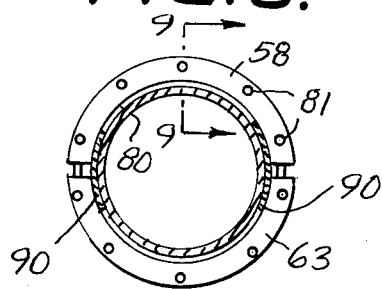
FIG. 8 is a transverse vertical cross-sectional view taken substantially on the line 8—8 of FIG. 7.

FIGS. 7, 8 and 9 illustrative another embodiment of a supporting fixture according to the present invention, designed to support a composite pipe section comprising two end elbow portions 13 connected by a straight intermediate portion 80. The supporting fixture thus comprises respective elbow-receiving mating pairs of cradle sections 51, 52 similar to that described in connection with FIGS. 4, 5 and 6, the cradle segments being connected at their inner ring flange portions 58, 59 and 63, 64 by respective longitudinally extending tie rods 81, 81 located on opposite sides of the straight pipe section 80. A sealing end flange plate member 31 is connected to the ends of one set of cradle segments 51, 52 and another sealing end flange plate member 32 is connected to the opposite end of the fixture, namely, to the ends of the opposite pair of cradle segments 51, 52, in the manner above described in connection with FIGS. 4, 5 and 6. Sealing of the ends of the composite pipe section may be achieved by suitably tensioning the tie rods 81 or by tightening the end flange fastening bolts 39, as above described. Any desired number of tension rods 81 may be employed. For example, a plurality of tension rods 81 may be employed spaced around the periphery of the intermediate pipe section 80 at equal angular spacings around the axis of the straight pipe section.

As is further shown in FIGS. 7, 8 and 9, throw-away pads 90 of heat-insulating and preferably resiliently deformable material may be employed between the cradle segments and the pipe section, particularly near the welded joints 91 of the composite pipe section, as shown in FIG. 9, to protect the pipe section against mechanical or heat damage. The procedure of installing the composite pipe section in the supporting fixture consists of first engaging the opposite elbows 13,13 between their associated cradle segments, fastening the pairs of cradle segments together, and then connecting the cradle segments by the tie rods 81. The end flange members 31 and 32 may be secured to the ends of respective pairs of cradle sections by means of the bolts 39, in the manner above described, and the sealing of the pipe section may be achieved by tightening the tie rods 81 and the bolts 39 in the manner above described. After this the necessary connections to the source of pressure-testing fluid and the required instruments can be made at the conduit fitting 43, as previously described.

While certain specific embodiments of improved supporting fixtures for pressure-testing pipe sections have been disclosed in the foregoing description, it will be understood that various modifications within the spirit of the invention may occur to those skilled in the art. Therefore, it is intended that no limitations be placed on the invention except as defined by the scope of the appended claims.

What is claimed is:

1. A supporting fixture for receiving and pressure testing a pipe section open at both ends in which the pipe section has an elbow portion at one end, said fixture comprising:
   a. a pair of curved rigid cradle members complementary to the curved contour of the elbow portion;
   b. means for securing the cradle members together against the elbow portion at said one end to form a rigid cage about the elbow portion to thereby prevent bending deflection of the elbow when the pipe section is pressurized;
   c. said cradle members having complementary semicircular ring flange members that transversely encircle the elbow portion adjacent said one end of the pipe section;
   d. a first pressure test end plate flange sealingly mounted over said one end to enclose said one end;
   e. clamping elements extending between the pressure test plate flange and the cradle ring flange members at angularly spaced locations about the elbow portion or uniformly clamping the first pressure test plate flange axially over said one end;
   f. a second pressure test end plate flange sealingly mounted over the other end of the pipe section; and
   g. tying means operatively interconnecting the second pressure test end plate flange and the cradle members axially along the pipe section to secure the second pressure test end plate flange firmly over the other end to enclose the other end to enable the pipe section to be pressure tested.

2. The supporting fixture of claim 1, and wherein each end plate flange member is provided with an annularly channeled seat shaped to receive the end of the pipe section therein and a resilient sealing gasket ring in the seat.

3. The supporting fixture of claim 2, and wherein each end plate flange member is generally circular and extends outwardly beyond its annular seat to define a securing marginal portion.

4. The supporting fixture of claim 1, and wherein each cradle segment comprises a plurality of spaced curved longitudinal ribs shaped to extend longitudinally parallel to the elbow portion and at least one cross bar member rigidly connected to said longitudinal ribs and shaped to substantially conform transversely with the contour of the elbow portion.

5. The supporting fixture of claim 1, and means longitudinally hinging the cradle segments together at one side.

6. The supporting fixture of claim 5, and wherein the means longitudinally hinging the cradle segments together is located adjacent the longer arcuate sides of the cradle segments.

7. The supporting fixture of claim 6, and wherein the cradle segments are provided at their longer arcuate sides with respective outwardly extending flanges having straight parallel edges and the hinging means comprises a linear hinge assembly connecting said parallel edges.

8. The supporting fixture of claim 1, and wherein the pipe section has a straight portion at the other end and wherein the fixture further comprises a pair of auxiliary cradle segments formed to conformably receive the straight portion of the pipe section therebetween, said second end plate flange member being secured to ends of said auxiliary segments and being formed to sealingly engage the end of said straight portion, and wherein the tying means includes longitudinal tie rod members connecting said auxiliary cradle segments to said first-named cradle segments.

9. The supporting fixture of claim 1 wherein the pipe section includes a second elbow portion at the other end and wherein the fixture further comprises an auxiliary pair of longitudinally arcuately curved cradle segments formed to conformably receive the second pipe elbow therebetween, said second end plate flange members being secured to ends of said auxiliary segments and being formed to sealingly engage the end of said second pipe elbow portion, and wherein the typing means includes longitudinal tie rod means connecting said auxiliary cradle segments to said first-named cradle segments.

* * * * *